United States Patent
Seo et al.

(10) Patent No.: US 9,835,553 B2
(45) Date of Patent: Dec. 5, 2017

(54) METHOD FOR SENING RESIDUES USING TERAHERTZ ELECTROMAGNETIC WAVES WITH HIGH SENSITIVITY AND DEVICE USED THEREFOR

(71) Applicant: KOREA INSTITUTE OF SCIENCE AND TECHNOLOGY, Seoul (KR)

(72) Inventors: Min-Ah Seo, Seoul (KR); Dong-Kyu Lee, Seoul (KR); Chul-Ki Kim, Seoul (KR); Taik-Jin Lee, Seoul (KR); Jae-Hun Kim, Seoul (KR); Young-Min Jhon, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 15/079,996

(22) Filed: Mar. 24, 2016

(65) Prior Publication Data

US 2017/0082540 A1    Mar. 23, 2017

(30) Foreign Application Priority Data

Sep. 23, 2015  (KR) .................. 10-2015-0134860

(51) Int. Cl.
  *G01N 21/3581* (2014.01)
  *G01N 33/02* (2006.01)
  *G01N 33/00* (2006.01)

(52) U.S. Cl.
  CPC ..... *G01N 21/3581* (2013.01); *G01N 33/0098* (2013.01); *G01N 33/02* (2013.01)

(58) Field of Classification Search
  CPC ....... G01N 2021/0346; G01N 21/6486; G01N 21/94; G01N 27/622; G01N 21/581; C07K 14/00
  See application file for complete search history.

(56) References Cited

U.S. PATENT DOCUMENTS

| 2011/0024630 A1* | 2/2011 | Sundaram | G01N 21/552 250/339.08 |
| 2013/0090263 A1* | 4/2013 | Tozer | G01N 21/6486 506/18 |

FOREIGN PATENT DOCUMENTS

KR        101050421 B1    7/2011

OTHER PUBLICATIONS

Xie, et al., Extraordinary sensitivity enhancement by metasurfaces in terahertz detection of antibiotics, Scientific Reports, Mar. 2, 2015, pp. 1-5, vol. 5 : 8671 | DOI: 10.1038/srep08671.

(Continued)

*Primary Examiner* — David Porta
*Assistant Examiner* — Faye Boosalis
(74) *Attorney, Agent, or Firm* — Goldilocks Zone IP Law

(57) ABSTRACT

Disclosed herein are a method and device for sensing pesticide residues, using terahertz electromagnetic waves. By the method, even a trace amount of pesticide residues on objects such as fruits can be accurately discriminated and sensed, with high sensitivity and selectivity, using a sensing chip that works in a terahertz electromagnetic wave band. Using the method, pesticide residues even at low concentrations can be accurately analyzed with high sensitivity and selectivity in which terahertz electromagnetic waves are irradiated onto pesticide residues through a sensing chip having a meta unit in which a pattern is formed to amplify a frequency corresponding to an absorption frequency of a pesticide residue of interest.

7 Claims, 5 Drawing Sheets

(56) References Cited

OTHER PUBLICATIONS

Tao, et al., A metamaterial absorber for the terahertz regime: Design, fabrication and characterization, Optical Society of America, May 2, 2008, pp. 7181-7188, vol. 16, No. 10.

* cited by examiner

METHOD FOR SENING RESIDUES USING TERAHERTZ ELECTROMAGNETIC WAVES WITH HIGH SENSITIVITY AND DEVICE USED THEREFOR

CROSS REFERENCE TO RELATED APPLICATION

The present application claims the benefit of Korean Patent Application No. 10-2015-0134860 filed on Sep. 23, 2015.

BACKGROUND OF THE INVENTION

1. Field of the Invention

The present disclosure relates to a method and device for sensing pesticide residues, using terahertz electromagnetic waves. Particularly, the present disclosure relates to a method by which even a trace amount of pesticide residues can be accurately detected and discriminated, with high sensitivity and selectivity, using a sensing chip that works in a terahertz electromagnetic wave band, and to a device therefor. Also, the present disclosure relates to a method for sensitively and selectively sensing pesticide residues even at low concentrations, in which terahertz electromagnetic waves are irradiated onto pesticide residues through a sensing chip having a meta unit in which a pattern is formed to amplify a frequency corresponding to an absorption frequency of a pesticide residue of interest, thus allowing for the quantitative analysis of pesticide residues, and a device therefor.

2. Description of the Related Art

Pesticide residue refers to the pesticides that may remain on or in foods, crops, or environments such as soil, rivers, etc., after they are applied to food crops to protect them from diseases and insects. In contrast to outdated farming approaches that paid attention only to higher productivity of crops, contemporary farming approaches, due largely to an increase in income levels and growing concerns with health, are concerned with the safe management of food crops, such as the measurement of pesticide residues.

On the whole, the analysis of pesticide residues is performed through extraction, purification, and instrumental analysis, as described in the following patent document.

Patent Document

Korean Patent No. 10-1050421 (issued Jul. 13, 2011) "Kit for Detecting Pesticide residues and the Detecting Method Thereof"

However, conventional methods of analyzing pesticide residues require much time for extraction, purification, and instrumental analysis, and the extraction process is performed only with selected samples because a complete enumeration survey is impossible.

Accordingly, a technique is required for allowing for the rapid measurement of pesticide residues. In addition, there is an urgent need for a technique by which even a trace amount of pesticide residues on food crops such as fruits can be accurately and rapidly detected.

SUMMARY OF THE INVENTION

Accordingly, the present invention has been made keeping in mind the above problems occurring in the related art, and an object of the present disclosure is to provide a method by which even a trace amount of pesticide residues on an object such as a fruit can be accurately detected and discriminated, with high sensitivity and selectivity, using a sensing chip that works in a terahertz electromagnetic wave band, and a device therefor.

Another object of the present disclosure is to provide a method for accurately analyzing pesticide residues by measuring changes in transmittance and frequency shift of the light reflected from the target pesticide residues through a sensing chip, and a device therefor.

A further object of the present disclosure is to provide a device in which the meta unit of the sensing chip formed on a flexible substrate can be applied to a curved surface, allowing pesticide residues on an object of any shape to be analyzed.

In order to accomplish the above objects, a method and a device for sensitively and selectively sensing pesticide residues using terahertz electromagnetic waves, have the following constitutions.

An aspect of the present disclosure provides a method for sensitively and selectively sensing pesticide residues, using a sensing chip, wherein the sensing chip has a meta unit in which a pattern is formed for amplifying a frequency corresponding to an absorption frequency of a pesticide residue of interest, and wherein the sensing chip, when irradiated with terahertz electromagnetic waves, passes the waves therethrough to the pesticide residue of interest and amplifies waves reflected from the pesticide residue of interest, whereby the pesticide residue of interest can be analyzed for subtype even when it is present at a low concentration.

In some embodiments, the method comprises: a target disposition step in which a pesticide residue of interest is disposed on a sensing chip having a meta unit in which a pattern is formed for amplifying a frequency corresponding to an absorption frequency of an pesticide residue of interest; a light irradiation step in which terahertz electromagnetic waves are irradiated to the pesticide residue of interest on the meta unit; and a target determination step in which the terahertz electromagnetic waves passing through the sensing chip are measured for transmittance or frequency change to specify the pesticide residue.

In a particular embodiment, the target determination step is adapted to measure the terahertz electromagnetic waves passing through the meta unit for transmittance or frequency change thus to specify pesticide residues and to determine concentrations of the specified pesticide residues, based on the fact that transmittance or a frequency change is elevated when the absorption frequency of a target pesticide residue corresponds to the resonant transmission frequency of the meta unit.

In a particular embodiment, the method further comprises: a quantitative analysis step in which the pesticide residue of interest is quantitatively analyzed, based on a change of the transmittance and/or frequency of the terawave passing through the sensing chip with a concentration of the pesticide residue of interest.

In a particular embodiment, the pattern is in a form of slits, each ranging in width from 10 nm to 1 µm, in thickness from 100 nm to 1 µm, and in length from 10 µm to 1 mm.

In a particular embodiment, the pattern is an array of slits that is formed at regular gaps in the meta unit of 1 nm to 1 mm in a widthwise direction and 1 nm to 1 mm in a lengthwise direction.

In a particular embodiment, the metal unit of the sensing chip is formed on a flexible substrate whereby the sensing chip can be applied to a curved surface of an object.

An aspect of the present disclosure provides a device for sensing pesticide residues, using the sensing chip used in the method of claim 7.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Below, a description will be given of some embodiments of the present invention in conjunction with the accompanying drawings. Unless otherwise defined, the meaning of all terms including technical and scientific terms used herein is the same as that commonly understood by one of ordinary skill in the art to which the present invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein. It should be apparent to those skilled in the art that although many specified elements such as concrete components are elucidated in the following description, they are intended to aid the general understanding of the invention and the present invention can be implemented without the specified elements. Further, in the description of the present invention, when it is determined that the detailed description of the related art would obscure the gist of the present disclosure, the description thereof will be omitted. Unless the context clearly requires otherwise, throughout the description and the claims, the words "comprise", "comprising", and the like are to be construed in an inclusive sense as opposed to an exclusive or exhaustive sense, that is to say, in the sense of "including, but not limited to."

The present disclosure addresses a method for sensitively and selectively sensing pesticide residues, using terahertz electromagnetic waves. The method is described in detail with reference to FIGS. 1 to 6. The method is adapted to qualitatively and quantitatively analyze even a trace amount of pesticide residues with high sensitivity and selectivity, in which terahertz electromagnetic waves (hereinafter referred to as "terawaves") are irradiated onto pesticide residues through a sensing chip 1 having a meta unit 11 in which a pattern is formed to amplify a frequency corresponding to an absorption frequency of a pesticide residue of interest.

Figure 4:
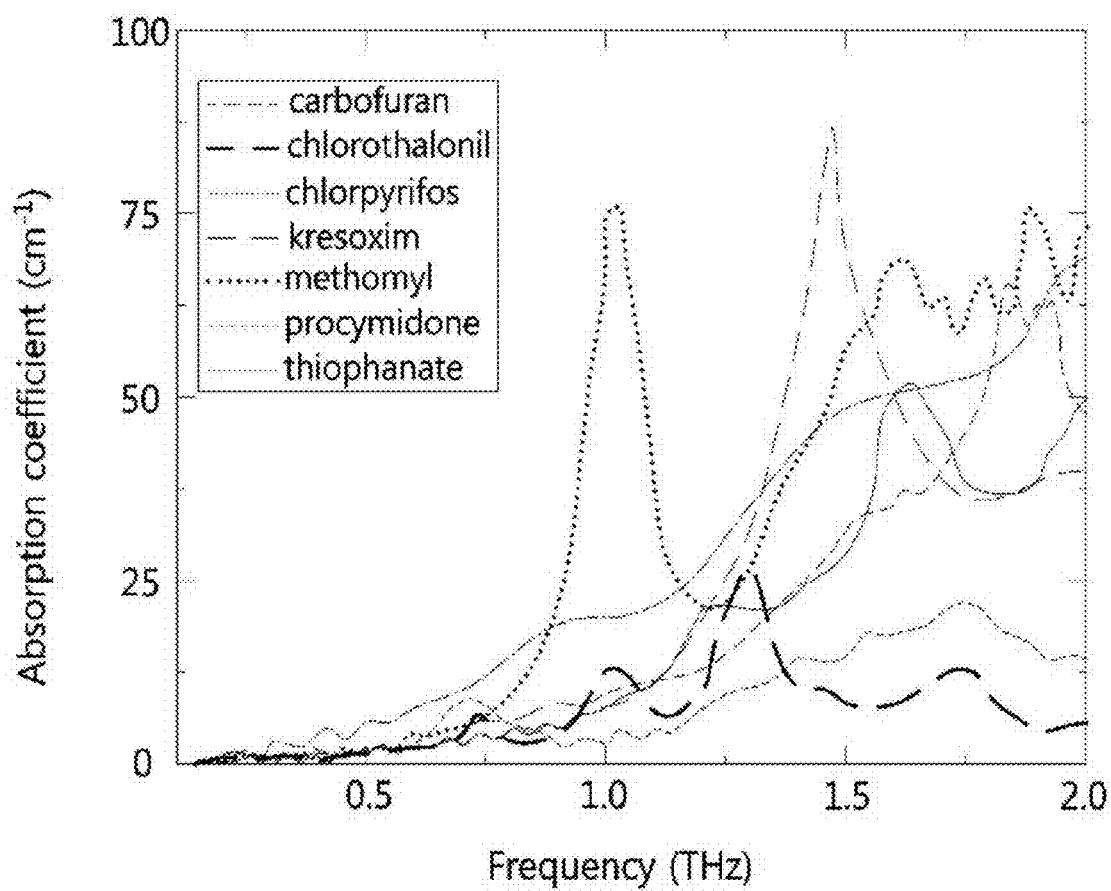
FIG. 4 is a view showing absorption spectra in a terahertz frequency band of various pesticides.

As described above, it is very difficult to selectively discriminate pesticide residues and to measure the amount of the specified pesticide residue. In the present disclosure, a sensing chip 1 having a meta unit 11 in which patterns are formed to amplify an absorption frequency of a pesticide of interest is used to irradiate terawaves onto pesticide residues in respective low amounts (concentrations) and to selectively measure even a trace amount (or concentration) of the pesticide of interest. Pesticides have various components. As shown in FIG. 4, they show respective characteristic absorption spectra in a terahertz frequency band. For example, absorption peaks are read at 1.0 THz for methomyl and at 1.5 THz for kresoxim. To selectively measure the concentration of a pesticide of interest even when its concentration is low, the present disclosure takes advantage of the fact that pesticides exhibit respective characteristic absorption peaks in a terahertz frequency band. In this regard, a meta unit 11 is designed such that it transmits terawaves and amplifies a frequency corresponding to the characteristic absorption frequency of a pesticide of interest. Based on this principle, a target can be selectively measured among various pesticides, and can be quantitatively analyzed even in a trace amount (or at a low concentration).

Now, a description will be given of a device useful in the method for sensing pesticides. The device comprises a sensing chip 1 having a meta unit 11 that works in a terawave range, an irradiator (not shown) for irradiating terawaves onto the sensing chip 1, a detector (not shown) for measuring a transmittance and/or a frequency change of the terawaves passing through the sensing chip 1 to specify pesticides and to determine concentrations of the specified pesticides.

The sensing chip 1 is configured to work in a terawave range, and comprises a meta unit 11 in which a pattern is formed to selectively amplify a frequency of interest, and a transparent substrate 12 for supporting the meta unit 11.

Figure 5:
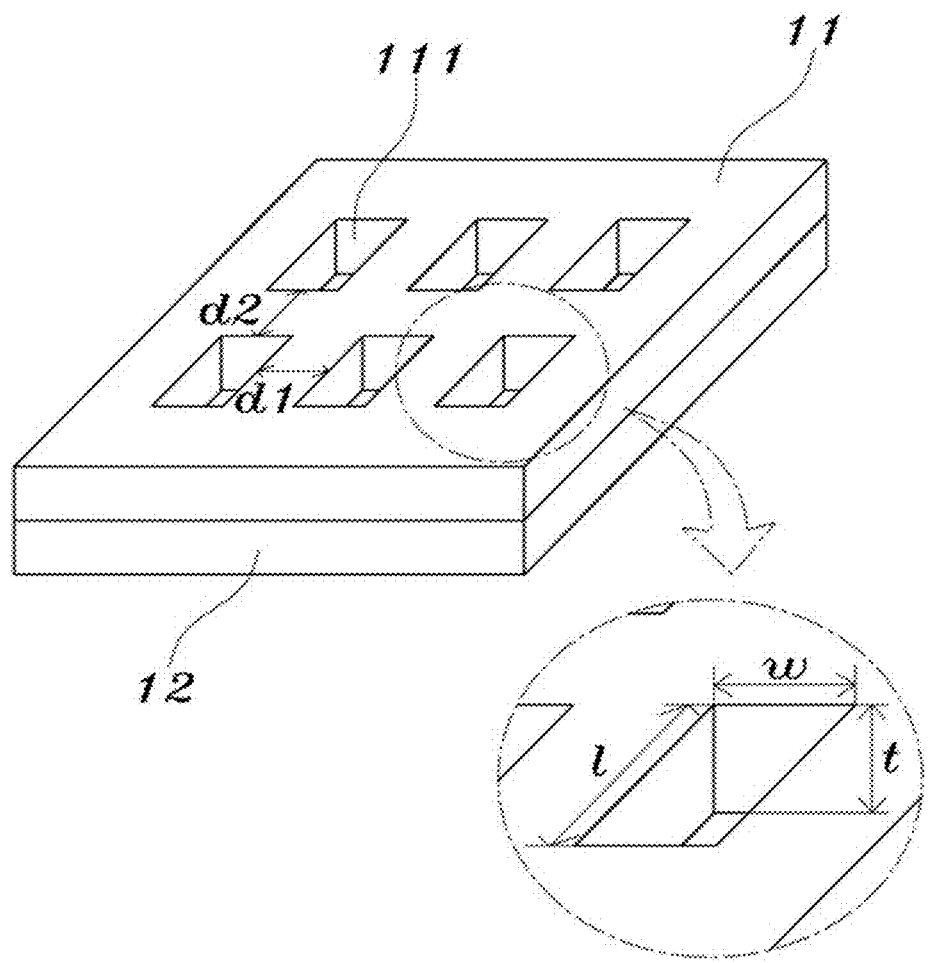
FIG. 5 is a perspective view of a sensing chip used in a method for sensing pesticide residues in accordance with an embodiment of the present disclosure.

The meta unit 11 is configured to have a pattern 111 for selectively amplifying a frequency of interest. For example, the pattern 111 may be an array of slits that is formed at regular gaps in the meta unit, each penetrating through the meta unit, as shown in FIG. 5. The meta unit 11 may be preferably made of a metallic material, such as gold, silver, copper, aluminum, etc., and is flexible with elasticity. In the pattern 111, the slits are constant in shape, size, and gap (hereinafter referred to as "spec"). Preferably, the slits range in width from (w) 10 nm to 1 μm, in thickness (t) from 100 nm to 1 μm, and in length (l) from 10 μm to 1 mm, with gaps of 1 nm to 1 mm therebetween in both the widthwise direction (d1) and the lengthwise direction (d2). The sensing chip 1 may be designed to amplify a specific frequency by adjusting the material of the meta unit 11 and/or the spec of the pattern 111 to set the resonance transmission frequencies of the sensing chip 1. Concrete examples are described, below.

In a particular embodiment of the present disclosure, the substrate 12, positioned beneath one side of the meta unit 11 to support the meta unit 11, is made of a transparent material, such as quartz, silicon, sapphire, glass, etc. Also, the sensing chip 1 may be designed to readily bend with elasticity so that it can be applied to a curved surface such as the surface of an apple. To this end, the substrate 12 may be made of a flexible material (for example, a synthetic resin with elasticity.

The irradiator irradiates onto the sensing chip 1 terahertz electromagnetic waves with a frequency of, for example, 0.1 to 5 THz. The detector is provided for measuring a transmittance and/or a frequency change of the terawaves passing through the sensing chip 1 to specify pesticides and to determine concentrations of the specified pesticides. After the sensing chip 1 is positioned on the surface of a target, such as a food crop or a target pesticide sample is loaded on the meta unit 11 of the sensing chip 1, terawaves are irradiated from the irradiator onto the sensing chip 1, and the detector measures the transmittance or frequency change of the terawaves passing through the sensing chip 1 to specify pesticides and to determine concentrations of the specified pesticides.

Turning to the method for sensing pesticides using the device described above with reference to FIG. 1, it comprises a target disposition step in which a pesticide of interest is distributed on a sensing chip 1 having a meta unit 11 in which a pattern is formed for selectively amplifying a specific frequency, a light irradiation step in which terahertz electromagnetic waves are irradiated to the pesticide of interest on the meta unit 11, and a pesticide determination step in which the terahertz electromagnetic waves passing through the sensing chip 1 are measured for transmittance or frequency change to specify pesticides and to determine concentrations of the specified pesticides. In accordance with some embodiments, the method may be applied to the analysis of pesticide residues that remain in liquid samples, such as from rivers, beverages, fruit juices, etc.

The target disposition step is a step in which a pesticide of interest (sample) is distributed on the sensing chip 1 having the meta unit 11 in which a pattern is formed for selectively amplifying a specific frequency. A pesticide to be analyzed is distributed on the meta unit 11 of the sensing chip 1 through which a resonant transmission frequency corresponding to the absorption frequency of a pesticide of interest is emitted. To specify methomyl, a sample is distributed on the meta unit 11 of the sensing chip 1 from which a resonant transmission frequency corresponding to the absorption frequency of methomyl is emitted. In the target disposition step, samples are placed on sensing chips 1 that are respectively designed according to pesticide components to be analyzed.

In the light irradiation step, terahertz electromagnetic waves are irradiated onto the target pesticides (samples) on the meta unit 11. In this regard, the irradiator emits a terawave with a frequency of 0.1 to 5 THz.

In the target determination step, the terahertz electromagnetic waves passing through the sensing chip 1 are measured for transmittance or frequency change to specify pesticides. Based on the fact that transmittance or frequency change is elevated when the absorption frequency of a target pesticide corresponds to the resonant transmission frequency of the meta unit, the pesticide can be specified. On the assumption, by way of example, that methomyl is present in a sample, a sensing chip manufactured to emit a resonant transmission frequency corresponding to the absorption frequency of methomyl may be employed to detect a large change in the transmittance and/or frequency of the terawave (change to a predetermined degree or more). When kresoxim is assumed to exist in a sample, the sensing chip designed to emit a resonant transmission frequency corresponding to the absorption frequency of methomyl can detect a small change in the transmittance and/or frequency of the terawave (change less than a predetermined degree). The pesticide can thus be specified in consideration of the change in the transmittance and/or frequency of the terawave passing the sensing chip 1.

Figure 6:
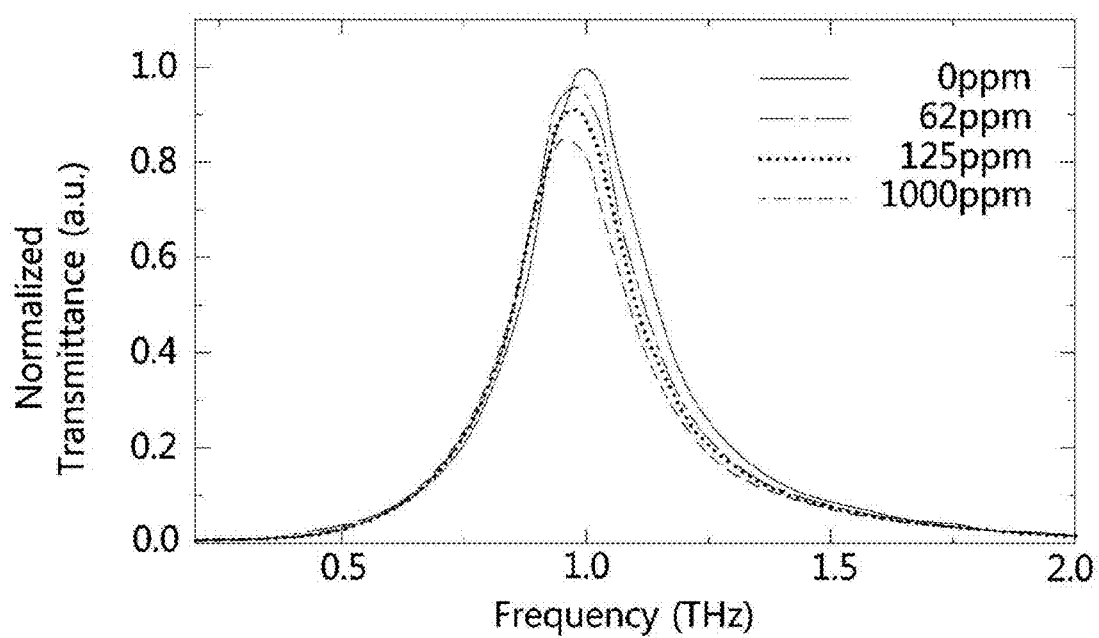
FIG. 6 is a graph showing measurement results of methomyl by using the sensing method of FIG. 1.

In another embodiment of the present disclosure, the method may further comprise a quantitative analysis step in which the pesticide of interest is quantitatively analyzed, based on a change in the transmittance and/or frequency of the terawave passing through the sensing chip with the concentration of the pesticide of interest. Because the transmittance and frequency vary with the concentration of a pesticide of interest, the magnitude of the transmittance and frequency shift of the terawave detected from the sensing chip allows for determining and providing the quantitative data of the pesticide of interest. For instance, a sensing chip (substrate made of silicon 500 μm thick, a meta unit made of gold 130 nm thick, and a pattern 500 nm wide, 60 μm long, and 130 nm thick) was manufactured to emit a resonant transmission frequency corresponding to the absorption frequency of methomyl, and one drop of a sample (comprising a buffer (PBS) and 0, 62, 125, or 1000 ppm methomyl) was added onto the meta unit 11 of the sensing chip 1. Then, terawaves were irradiated onto the sample, followed by measuring the transmittance and frequency change of the terawaves passing through the sensing chip 1. The measurement results are depicted in FIG. 6 (in which NA accounts for terawaves that were irradiated onto the sensing chip 1 with no samples placed on the chip). As can be seen in FIG. 6, the transmittance and the frequency vary with the concentration of methomyl. Thus, the magnitude of the transmittance and frequency shift of the terawave detected from the sensing chip allows for the quantitative analysis of pesticide residues.

Figure 1:
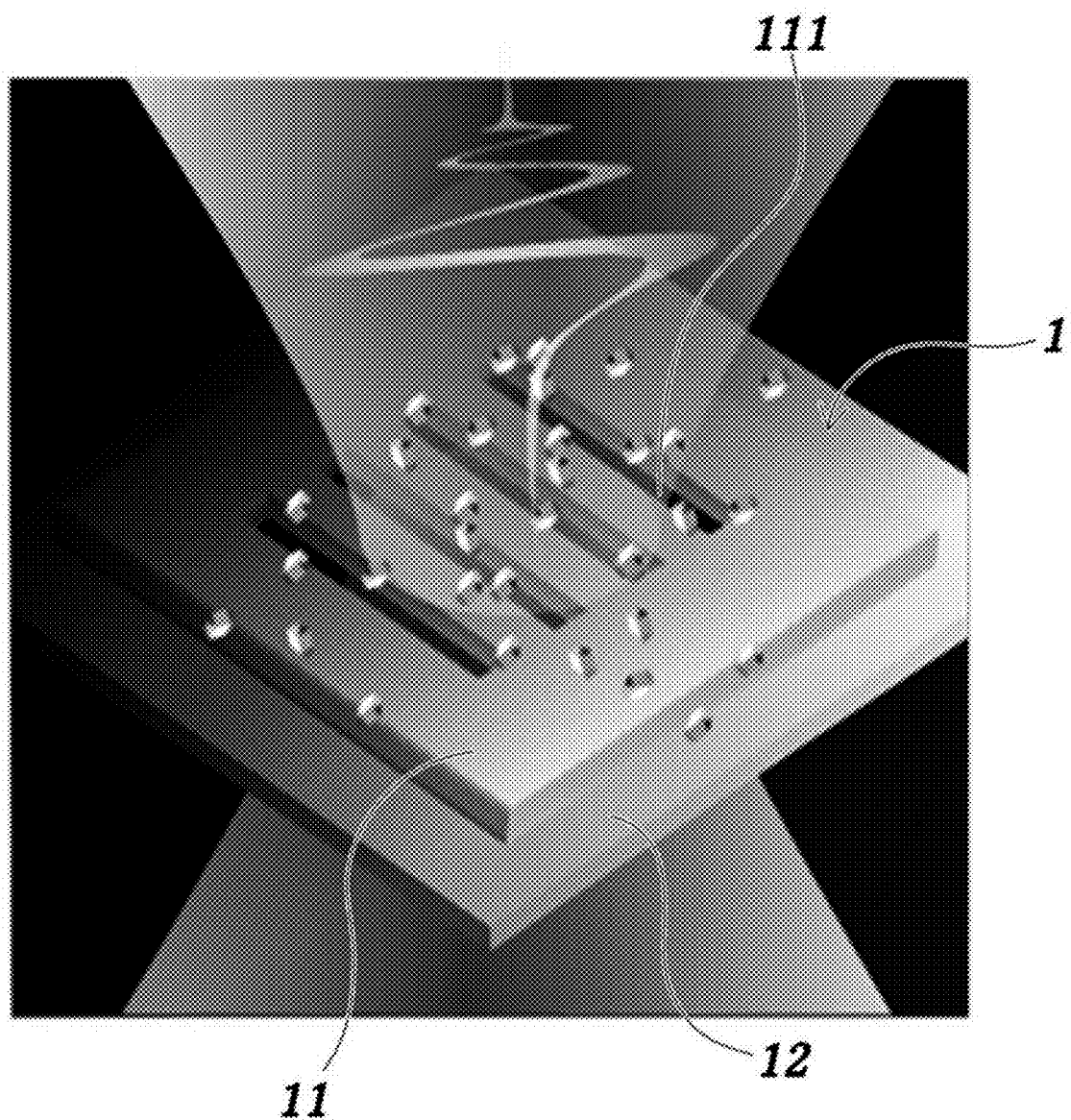
FIG. 1 is a view illustrating a method for sensing pesticide residues in accordance with an embodiment of the present disclosure.
Figure 2:
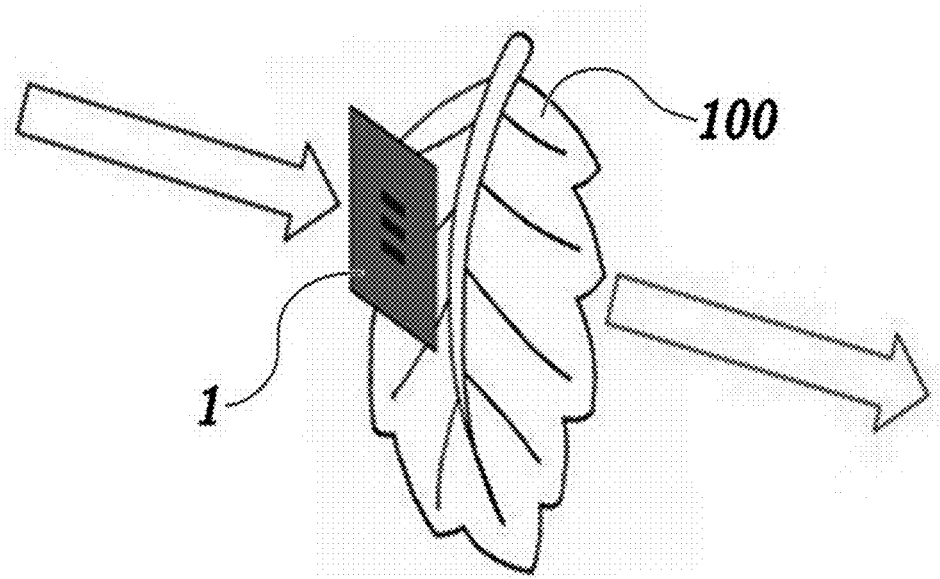
FIG. 2 is a view illustrating a method for sensing pesticide residues in accordance with another embodiment of the present disclosure.
Figure 3:
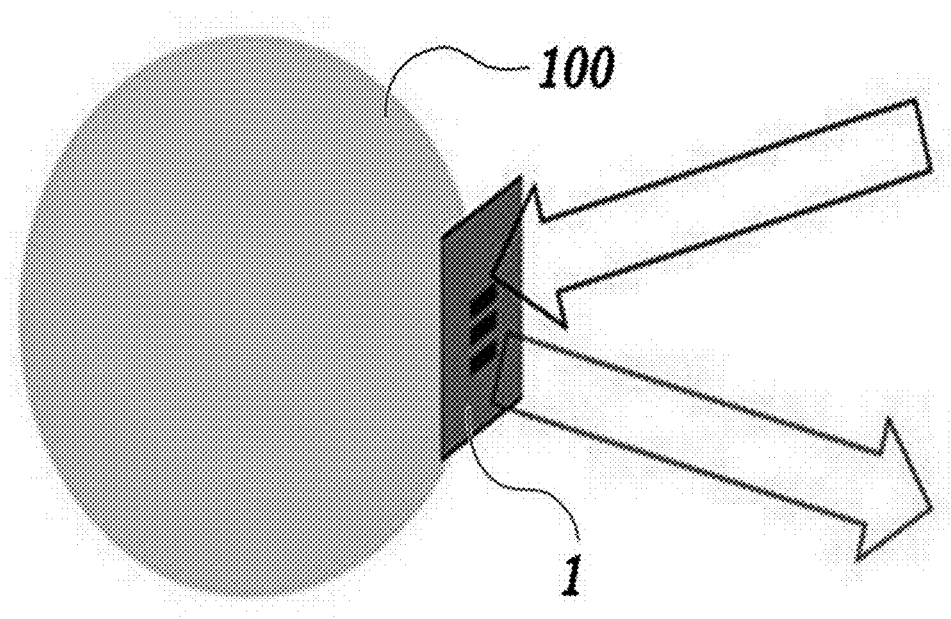
FIG. 3 is a view illustrating a method for sensing pesticide residues in accordance with a further embodiment of the present disclosure.

A method for sensing pesticides using the foregoing technical spirit and the device in accordance another embodiment is described with reference to FIGS. 2 and 3. The method comprises a target disposition step in which the sensing chip 1 having a meta unit 11 provided with a pattern for selectively amplifying a specific frequency is positioned on an object 100 on which a pesticide of interest is present; a light irradiation step in which terahertz electromagnetic waves are irradiated onto the meta unit 11; a target determination step in which terahertz electromagnetic waves that are reflected from the object 100 and pass through the sensing chip 1 are measured for transmittance or frequency change to specify the pesticide; and a quantitative analysis step in which the pesticide of interest is quantitatively analyzed, based on a change in the transmittance and/or frequency of the terawave passing through the sensing chip with the concentration of the remaining pesticide. From the aforementioned method in which a sample (pesticide) is dropped on the meta unit 11 and terawaves are irradiated, followed by detecting the transmittance and frequency shift of the terawaves passing the sensing chip 1, this method is different only in the steps of positioning the sensing chip 1 on the skin of food crops such as apples, pears, lettuce, etc., irradiating terawaves onto the object through the sensing chip 1, and detecting the transmittance and frequency shift of terawaves that penetrate through the object (for example leaves such as lettuce) as shown in FIG. 2 or are reflected from the object (for example, apples, pears, etc.) through the sensing chip 1 as shown in FIG. 3 so as to specify a pesticide and to determine the concentration of the specified pesticide. The two methods are based on the same principle that a sensing chip from which a resonant transmission frequency corresponding to an absorption frequency of a pesticide of interest can be emitted is utilized to specify a pesticide residue and determine the concentration of the pesticide through the amplification of terawaves. Hence, a detailed description relevant to the principle is omitted. The method according to this embodiment allows various pesticide residues to be analyzed without destroying food crops.

As described in the foregoing embodiments and constitutional elements of the present disclosure, and their combinations, the present invention enjoys the following advantages.

The method and device according to the present invention can rapidly sense a pesticide residue on an object such as a fruit, with high sensitivity and selectivity, using terahertz electromagnetic waves, even though a trace amount of a sample is present.

Also, capable of determining the concentration of pesticide residues in response to the magnitude of the transmittance and frequency change of the light detected through the sensing chip, the method and device according to the present invention can find applications in the quantitative analysis of pesticide residues.

Further, the device in which the meta unit of the sensing chip is formed on a flexible substrate can be applied to a curved surface, allowing pesticide residues on an object of any shape to be analyzed.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for sensitively and selectively sensing pesticide residues, using a sensing chip, wherein the sensing chip has a meta unit in which a pattern is formed for amplifying a frequency corresponding to an absorption frequency of a pesticide residue of interest, and wherein the sensing chip, when irradiated with terahertz electromagnetic waves, passes the waves therethrough to the pesticide residue of interest and amplifies waves reflected from the pesticide residue of interest, whereby the pesticide residue of interest can be analyzed for subtype even when it is present at a low concentration, wherein the method comprises:
   a target disposition step in which a pesticide residue of interest is disposed on a sensing chip having a meta unit in which a pattern is formed for amplifying a frequency corresponding to an absorption frequency of a pesticide residue of interest;
   a light irradiation step in which terahertz electromagnetic waves are irradiated to the pesticide residue of interest on the meta unit; and
   a target determination step in which the terahertz electromagnetic waves passing through the sensing chip are measured for transmittance or frequency change to specify the pesticide residue.

2. The method of claim 1, wherein the target determination step is adapted to measure the terahertz electromagnetic waves passing through the meta unit for transmittance or frequency change thus to specify pesticide residues and to determine concentrations of the specified pesticide residues, based on the fact that transmittance or a frequency change is elevated when the absorption frequency of a target pesticide residue corresponds to the resonant transmission frequency of the meta unit.

3. The method of claim 1, further comprising:
   a quantitative analysis step in which the pesticide residue of interest is quantitatively analyzed, based on a change of the transmittance and/or frequency of the terawave passing through the sensing chip with a concentration of the pesticide residue of interest.

4. The method of claim 1, wherein the pattern is in a form of slits, each ranging in width from 10 nm to 1 μm, in thickness from 100 nm to 1 μm, and in length from 10 μm to 1 mm.

5. The method of claim 4, wherein the pattern is an array of slits that is formed at regular gaps in the meta unit of 1 nm to 1 mm in a widthwise direction and 1 nm to 1 mm in a lengthwise direction.

6. The method of claim 4, wherein the metal unit of the sensing chip is formed on a flexible substrate whereby the sensing chip can be applied to a curved surface of an object.

7. A device for sensing pesticide residues, using the sensing chip used in the method of claim 6.

* * * * *